(12) United States Patent
Edelman et al.

(10) Patent No.: US 10,188,665 B2
(45) Date of Patent: *Jan. 29, 2019

(54) OCULAR THERAPY USING GLUCOCORTICOID DERIVATIVES SELECTIVELY PENETRATING POSTERIOR SEGMENT TISSUES

(71) Applicant: Allergan, Inc., Irvine, CA (US)

(72) Inventors: Jeffrey L. Edelman, Irvine, CA (US); Kelly M. Harrison, Harker Heights, TX (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,089

(22) Filed: Nov. 20, 2017

(65) Prior Publication Data
US 2018/0125861 A1    May 10, 2018

Related U.S. Application Data

(60) Division of application No. 15/043,750, filed on Feb. 15, 2016, now Pat. No. 9,820,995, which is a
(Continued)

(51) Int. Cl.
*A61K 9/00* (2006.01)
*A61K 31/573* (2006.01)
(Continued)

(52) U.S. Cl.
CPC .......... *A61K 31/573* (2013.01); *A61K 9/0048* (2013.01); *A61K 9/0051* (2013.01); *A61K 9/1647* (2013.01); *A61K 31/56* (2013.01); *A61K 31/728* (2013.01); *A61K 47/34* (2013.01); *A61K 47/36* (2013.01); *Y02A 50/401* (2018.01)

(58) Field of Classification Search
CPC .. A61K 9/0051; A61K 9/0017; A61K 9/1647; A61K 31/573
See application file for complete search history.

(56) References Cited

U.S. PATENT DOCUMENTS

| 4,521,210 A | 6/1985 | Wong |
| 4,853,224 A | 8/1989 | Wong |

(Continued)

FOREIGN PATENT DOCUMENTS

| JP | A-2004-210798 | 7/2004 |
| JP | A-7-309763 | 11/2007 |

(Continued)

OTHER PUBLICATIONS

U.S. Appl. No. 60/728,209, Edelman, filed Oct. 18, 2006.
(Continued)

*Primary Examiner* — Carlos A Azpuru
(74) *Attorney, Agent, or Firm* — Brigitte C. Phan

(57) ABSTRACT

Ophthalmically therapeutic materials, such as liquid-containing compositions and polymeric drug delivery systems, include a therapeutic component that includes an Glucocorticoid Derivative which, upon delivery to the posterior segment of a mammalian eye, does not significantly diffuse to the anterior segment of said eye. Methods of making and using the present materials are also described.

12 Claims, 7 Drawing Sheets

Related U.S. Application Data continuation of application No. 14/463,034, filed on Aug. 19, 2014, now Pat. No. 9,259,429, which is a continuation of application No. 13/299,215, filed on Nov. 17, 2011, now Pat. No. 8,840,872, which is a division of application No. 11/550,642, filed on Oct. 18, 2006, now Pat. No. 8,062,657.

(60) Provisional application No. 60/728,209, filed on Oct. 18, 2005.

(51) Int. Cl.
  *A61K 31/728* (2006.01)
  *A61K 9/16* (2006.01)
  *A61K 31/56* (2006.01)
  *A61K 47/36* (2006.01)
  *A61K 47/34* (2017.01)

(56) References Cited

U.S. PATENT DOCUMENTS

| | | | |
|---|---|---|---|
| 4,997,652 | A | 3/1991 | Wong |
| 5,164,188 | A | 11/1992 | Wong |
| 5,336,767 | A | 8/1994 | Della Valle et al. |
| 5,443,505 | A | 8/1995 | Wong |
| 5,501,856 | A | 3/1996 | Ohtori |
| 5,540,930 | A | 7/1996 | Guy et al. |
| 5,632,984 | A | 5/1997 | Wong |
| 5,646,136 | A | 7/1997 | Petrow et al. |
| 5,766,242 | A | 6/1998 | Wong |
| 5,770,589 | A | 6/1998 | Billson et al. |
| 5,824,072 | A | 10/1998 | Wong |
| 5,869,079 | A | 2/1999 | Wong |
| 6,074,661 | A | 6/2000 | Olejnik |
| 6,331,313 | B1 | 12/2001 | Wong |
| 6,369,116 | B1 | 4/2002 | Wong |
| 6,699,493 | B2 | 3/2004 | Wong |
| 6,726,918 | B1 | 4/2004 | Wong |
| 8,062,657 | B2 * | 11/2011 | Edelman .............. A61K 9/0048 424/428 |
| 8,840,872 | B2 | 9/2014 | Edelman |
| 9,259,429 | B2 | 2/2016 | Edelman |
| 2002/0182185 | A1 | 12/2002 | Wong |
| 2003/0060763 | A1 | 3/2003 | Penfold |
| 2004/0171598 | A1 | 9/2004 | Bingaman |
| 2005/0048099 | A1 | 3/2005 | Shiah et al. |
| 2005/0101582 | A1 | 5/2005 | Lyons |
| 2005/0244474 | A1 | 11/2005 | Huang et al. |
| 2007/0088014 | A1 | 4/2007 | Edelman et al. |

FOREIGN PATENT DOCUMENTS

| | | |
|---|---|---|
| WO | WO 98/19649 | 5/1998 |
| WO | WO 2004/050065 | 6/2004 |
| WO | WO 2004/073607 | 9/2004 |
| WO | WO 2005/046641 | 5/2005 |
| WO | WO2005/072701 | 8/2005 |
| WO | WO 2005/107727 | 11/2005 |

OTHER PUBLICATIONS

Edelman et al., Exp. Eye Res. 80:249-258 (2005).

Fiahlo, Silvia Ligorio et al., *Manufacturing Techniques of Biodegradable Implants Intended for intraocular Application*, Drug Delivery, Academic Press, Orlando, FL, vol. 12, No. 2, Apr. 2005, pp. 109-116.

Heller, Biodegradable Polymers in Controlled Drug Delivery, In: CRC Critical Reviews in Therapeutic Drug Carrier Systems, vol. 1, CRC Press, Boca Raton, FL 1987, pp. 39-90.

Hudson, Henry L., Retinal Physician Jul. 2005 (www.retinalphysician.com/ article.aspx?article=100098).

Missel, P.J. et al., *Dissolution of anecortave acetate in a cylindrical flow cell: re-evaluation of convective diffusion/drug dissolution for sparingly soluble drugs*, Pharmaceutical Development and Technology, vol. 9, No. 4, 2004, pp. 453-459.

Stokes et al, "Altered Peripheral Sensitivity to Glucocorticoids in Primary Open-Angle Glaucoma", Invest.Ophthalmol Vis Sci. 44, 5163-5167, 2003.

USP 23; NF 18 (1995) pp. 1790-1798.

Wu, W. et al., *Intravitreally injectable poly (D,L-/actide) microspheres containing deamethasone acetate for sustained release*, Biosciences Information Service, Philadelphia, PA, Oct. 2001, vol. 36, No. 10, pp. 766-770.

Acta Pharmaceutica Sinica, 2001, 36(10), 766-770.

Drug Delivery, 2005, 12(2), 109-116.

* cited by examiner

OCULAR THERAPY USING GLUCOCORTICOID DERIVATIVES SELECTIVELY PENETRATING POSTERIOR SEGMENT TISSUES

CROSS REFERENCE

The present application is a divisional of Ser. No. 15/043,750, filed Feb. 15, 2016, now U.S. Pat. No. 9,820,995, which is a continuation of U.S. patent application Ser. No. 14/463,034, filed Aug. 19, 2014, now U.S. Pat. No. 9,259,429, which is a continuation of U.S. patent application Ser. No. 13/299,215, filed on Nov. 17, 2011, now U.S. Pat. No. 8,840,872, which is a divisional application of U.S. patent application Ser. No. 11/550,642, filed on Oct. 18, 2006, now U.S. Pat. No. 8,062,657, which claims priority to the U.S. Provisional Patent Application Ser. No. 60/728,209, filed on Oct. 18, 2005, the entire contents of the preceding are hereby incorporated by reference.

BACKGROUND OF THE INVENTION

The mammalian eye is a complex organ comprising an outer covering including the sclera (the tough white portion of the exterior of the eye) and the cornea, the clear outer portion covering the pupil and iris. In a medial cross section, from anterior to posterior, the eye comprises features including, without limitation: the cornea, the anterior chamber (a hollow feature filled with a watery clear fluid called the aqueous humor and bounded by the cornea in the front and the lens in the posterior direction), the iris (a curtain-like feature that can open and close in response to ambient light) the lens, the posterior chamber (filled with a viscous fluid called the vitreous humor), the retina (the innermost coating of the back of the eye comprised of light-sensitive neurons), the choroid (and intermediate layer providing blood vessels to the cells of the eye), and the sclera. The posterior chamber comprises approximately ⅔ of the inner volume of the eye, while the anterior chamber and its associated features (lens, iris etc.) comprise about ⅓ of the eye's volume.

The delivery of therapeutic agents to the anterior surface of the eye is relatively routinely accomplished by topical means such as eye drops. However, the delivery of such therapeutic agents to the interior or back of the eye, even the inner portions of the cornea, presents unique challenges. Drugs are available that may be of use in treating diseases of the posterior segment of the eye, including pathologies of the posterior sclera, the uveal tract, the vitreous, the choroid, retina and optic nerve head (ONH).

However, a major limiting factor in the effective use of such agents is actually getting the agent to the affected tissue. The urgency to develop such methods can be inferred from the fact that the leading causes of vision impairment and blindness are posterior segment-linked diseases. These diseases include, without limitation, age-related macular degeneration (ARMD), proliferative vitreoretinopathy (PVR), diabetic macular edema (DME), and endophthalmitis. Glaucoma, which is often thought of as a condition of the anterior chamber affecting the flow (and thus the intraocular pressure (IOP)) of aqueous humor, also has a posterior segment component; indeed, certain forms of glaucoma are not characterized by high IOP, but mainly by retinal degeneration alone.

The present invention relates to the use of Glucocorticoid Derivatives (GDs) that are either selectively designed to possess the ability to be directed to tissue of the posterior segment of the eye, or which possess the ability, when administered to the posterior segment of the eye, to preferentially penetrate, be taken up by, and remain within the posterior segment of the eye, as compared to the anterior segment of the eye. More specifically, the invention is drawn to ophthalmic compositions and drug delivery systems that provide extended release of the Glucocorticoid Derivatives to the posterior segment (or tissue comprising within the posterior segment) of an eye to which the agents are administered, and to methods of making and using such compositions and systems, for example, to treat or reduce one or more symptoms of an ocular condition to improve or maintain vision of a patient.

Glucocorticoids are one of the three major classes of steroid hormones, the other two being the sex hormones and the mineralcorticoids. The naturally occurring glucocorticoids include cortisol (hydrocortisone), which is essential for the maintenance of life. Cortisol is a natural ligand to the glucocorticoid nuclear receptor, a member of the steroid superfamily of nuclear receptors, a very large family of receptors that also includes the retinoid receptors RAR and RXR, the peroxisome proliferator-activated receptor (PPAR), the thyroid receptor and the androgen receptor. Among other activities, cortisol stimulates gluconeogenesis from amino acids and lipids, stimulates fat breakdown and inhibits glucose uptake from muscle and adipose tissue.

Glucocorticoids can therefore be distinguished by their activity, which is associated with glucose metabolism, and by their structure. All steroid hormones derive their core structure from cholesterol, which has the following structure and numbering scheme.

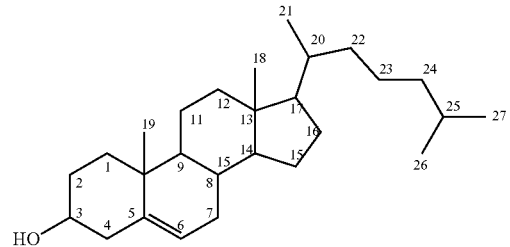 [SMILES: CC(C)CCCC(C)C1CCC2C3CC=C4CC(O)CCC4(C)C3CCC12C]

Glucocorticoids are large multiringed derivatives of cholesterol; the characteristics comprising a hydroxyl group at $C_{11}$, and/or a double bond between $C_4$ and $C_5$. The double bond between carbons 5 & 6 is not an essential part of a glucocorticoid, nor is the identity of any particular R group at $C_{17}$.

Corticosteroids are steroid hormones released by the adrenal cortex; they comprise the mineralcorticoids (the only naturally occurring mineralcorticoid is aldosterone) and the glucocorticoids. The term "corticosteroid" is sometimes used to mean glucocorticoid, and unless specifically indicated otherwise, this will be the meaning in this patent application. Exemplary glucocorticoids include, without limitation, dexamethasone, betamethasone, triamcinolone, triamcinolone acetonide, triamcinolone diacetate, triamcinolone hexacetonide, beclomethasone, dipropionate, beclomethasone dipropionate monohydrate, flumethasone pivalate, diflorasone diacetate, fluocinolone acetonide, fluorometholone, fluorometholone acetate, clobetasol propionate, desoximethasone, fluoxymesterone, fluprednisolone, hydrocortisone, hydrocortisone acetate, hydrocortisone butyrate, hydrocortisone sodium phosphate, hydrocortisone sodium succinate, hydrocortisone cypionate, hydrocortisone probutate, hydrocortisone valerate, cortisone acetate, paramethasone acetate, methylprednisolone, methylprednisolone acetate, methylprednisolone sodium succinate, prednisolone, prednisolone acetate, prednisolone sodium phosphate, prednisolone tebutate, clocortolone pivalate, flucinolone, dexamethasone 21-acetate, betamethasone 17-valerate, isofluredone, 9-fluorocortisone, 6-hydroxydexamethasone, dichlorisone, meclorisone, flupredidene, doxibetasol, halopredone, halometasone, clobetasone, diflucortolone, isoflupredone acetate, fluorohydroxyandrostenedione, beclomethasone, flumethasone, diflorasone, clobetasol, cortisone, paramethasone, clocortolone, prednisolone 21-hemisuccinate free acid, prednisolone metasulphobenzoate, prednisolone terbutate, triamcinolone acetonide 21-palmitate, prednisolone, fluorometholone, medrysone, loteprednol, fluazacort, betamethasone, prednisone, methylprednisolone, triamcinolone hexacatonide, paramethasone acetate, diflorasone, fluocinolone and fluocinonide, derivatives thereof, salts thereof, and mixtures thereof. Some of these compounds are GDs, as defined in this patent application, and others are prospective parents of such GDs.

In 1950 the Nobel Prize for Medicine was awarded to Hench, Kendall and Richenstein for their work concerning adrenal (naturally occurring) and synthetic glucocorticoids. Since that time these compounds including, without limitation, hydrocortisone and the synthetic glucocorticoids dexamethasone and prenisolone have been a valuable part of the physician's arsenal of weapons to fight inflammation, inflammatory diseases and conditions such as acute asthma.

The glucocorticoid receptor (GR) is found in almost all tissues of the mammalian body. The nuclear receptors, including the glucocorticoid receptor, are ligand-dependent transcription factors that, when activated, bind to chromosomal DNA and initiate or inhibit the transcription of particular genes. As a result, steroids have myriad effects on various systems of the body.

Historically, the short-term systemic or topical use of glucocorticoids has been largely free of serious side effects, and the therapeutic effects of such use are sometimes quite miraculous, particularly in treating diseases related to inflammation, such as arthritis and the like. However, because of the diverse and somewhat poorly characterized effects these compounds have, prolonged use of glucocorticoids, particularly prolonged systemic exposure to these agents, can give rise to a variety of sometimes serious side effects such as glucose intolerance, diabetes, weight gain, osteoporosis, and fat redistribution, as well as frailty and skin thinning.

The topical use of steroids in the treatment of ophthalmic conditions (particularly ocular inflammation) is also well known. Clinicians have found topical administration of steroids to be safe and effective for short-term use in the treatment of conditions of the anterior chamber of the eye. For moderate to severe inflammation loteprednol etabonate 0.5% (Lotemax®), prednisolone acetate (Pred Forte®), prednisolone sodium phosphate (Inflamase Forte®) and rimexolone (Vexol®) have been used with success, while the fluorometholones are prescribed for mild to moderate inflammation—additionally, dexamethosone and hydrocortosone are also used for topical ocular use. Triamcinolone (Kenalog 50®—approved for dermatological use) has been successfully used as an off-label medication for intravitreal injection for the treatment of macular edema.

All of the above-mentioned topical steroid preparations are designed and/or used mainly for superficial or anterior segment inflammation. However, topical application of steroid drugs does not result in significant concentrations of the drug entering the posterior segment. Indeed, only a minute fraction of the drug topically applied to the surface of the eye ends up within the eye, with the majority of what drug does enter the eye remaining contained within the anterior segment. Retisert®, is a non-biodegradable implant for delivery to the posterior segment. It comprises fluocinolone acetonide, and has been approved for the treatment of chronic noninfective posterior uveitis. Retisert® has also been associated with 90.3% of study eyes developing cataracts, necessitating surgical removal. See Hudson, Henry L., Retinal Physician July 2005 (www.retinalphysician.com/article.aspx?article=100098), incorporated herein by reference. Some ophthalmologists have recently made use of the triamcinolone acetonide suspension Kenalog® 40 by injecting into the vitreous of patients suffering from conditions including, without limitation, cystic macular edema, diabetic macular edema, and wet macular degeneration. The few steroids, such as dexamethasone and triamcinolone acetonide that have been reported to be used intravitreally tend to migrate by diffusion to anterior segment tissues, which can cause serious and unwanted side effects.

Additionally, in May 2003 Oculex Pharmaceuticals announced that preliminary findings from a clinical trial testing a biodegradable intravitreal implant containing 700 µg of the corticosteroid dexamethasone showed that the implant, having the trade name Posurdex®, was highly effective in improving vision in patients suffering from persistent macular edema.

When treating conditions of the posterior segment with steroids it is particularly preferable to reduce the exposure of anterior segment tissues to steroids—long term use of steroids can lead to extremely high incidence of lens cataracts, ocular hypertension, and steroid-induced glaucoma.

In part, the present invention is drawn to methods of treating a variety of conditions of the posterior segment including (without limitation): cystic macular edema, diabetic macular edema, diabetic retinopathy, uveitis, and wet macular degeneration, by the administration of GDs, including $C_{17}$- and/or $C_{21}$-substituted GDs, to specifically target the tissue of the posterior segment of the eye, and to resist migration to the anterior segment. In other embodiments the invention is drawn to compositions comprising such glucocorticoid components and to methods of administrating such glucocorticoids.

In a particularly preferred embodiment a composition comprising one or more GD is administered directly to the posterior segment by, for example, injection or surgical incision. In a further embodiment the composition is injected directly into the vitreous humor in a fluid solution or suspension of crystals or amorphous particles comprising a GD compound. In another embodiment the composition is comprised within an intravitreal implant. The GD may, without limitation, be comprised in a reservoir of such implant, may be joined to a biodegradable implant matrix in such a manner that it is released as the matrix is degraded, or may be physically blended with the biodegradable polymeric matrix.

Additionally, while less preferred, a GD of the present invention may be administered to the posterior segment indirectly, such as (without limitation) by topical ocular administration, by subconjunctival or subscleral injection.

The GDs of the present invention all possess certain properties in accord with the present invention. First, the GD should possess a relatively slow dissolution rate. By "relatively low dissolution rate" is mean a dissolution rate from the solid to the vitreous liquid phase, which is less than that of triamcinolone acetonide preferably 50% or less of the dissolution rate of triamcinolone acetonide, even more preferably 25% or less than the dissolution rate of triamcinolone acetonide, 10% or less than that of triamcinolone acetonide.

Secondly, the GD should possess a relatively low solubility in the vitreous humor. By "relatively low solubility" is mean a solubility which is less than that of triamcinolone acetonide, preferably 50% or less of the dissolution rate of triamcinolone acetonide, even more preferably 25% or less than the dissolution rate of triamcinolone acetonide, or 10% or less than that of triamcinolone acetonide.

In another measurement of solubility, the GD used in the present invention has an aqueous solubility less than about 21 mg/ml, preferably less than about 10 mg/ml, even more preferably less than about 5 mg/ml, or less than about 2 mg/ml, or less than about 1 mg/ml, or less than about 0.5 mg/ml or less than about 0.2 mg/ml or less than about 0.14 mg/ml at room temperature and atmospheric pressure (sea level).

Finally, the GD should be highly lipophilic so as to partition well into the membranes of retinal tissue and quickly achieve a high local concentration of GD in retinal tissue. This means that a GD has a lipophilicity (log P, where P is the octanol/water partition coefficient) of greater than 2.53, or greater than 3.00, or greater than about 3.5 or greater than about 4.00, or greater than about 4.20 at room temperature and atmospheric pressure (sea level).

While a most preferred GD possesses all of these properties, a GD may possess less than all such properties so long as it possesses the property of remaining therapeutically active in the posterior chamber when delivered intravitreally, while not being present in therapeutically effective concentrations in the anterior chamber.

The vitreous chamber bathes the posterior surface of the lens and is connected to the anterior chamber via a fluid channel that encircles the lens and continues through the pupil. Solutes (including solublized glucocorticoids) in the vitreous may diffuse anteriorly to the lens, or around the lens to the anterior chamber outflow apparatus (the trabecular meshwork, Sclemm's canal), thereby causing steroid-induced cataracts, ocular hypertension or glaucoma.

The present inventors have found that steroids that are only sparingly soluble in vitreal fluid and that have a slow dissolution rate from the solid to the soluble form do not migrate well to the anterior segment. While not wishing to limit the scope of the invention by theory, and only as an illustration, the Applicants believe that the GDs of the present invention lack sufficient diffusional force due to their lack of solubility in the vitreous to move the soluble steroid through the indicated path to the anterior chamber. The lipophilicity of the GDs of the present invention, at the same time, encourages their partition from the aqueous vitreous fluid to the lipid bilayer of the retinal cell membranes. This is thought to create a low-level intravitreal flow of the GD from vitreous to retina, at a concentration sufficient to provide therapeutic benefit to the retinal tissue, but at a low enough level to confer substantially reduced exposure to the lens and anterior segment tissues.

DETAILED DESCRIPTION

Figure 1:
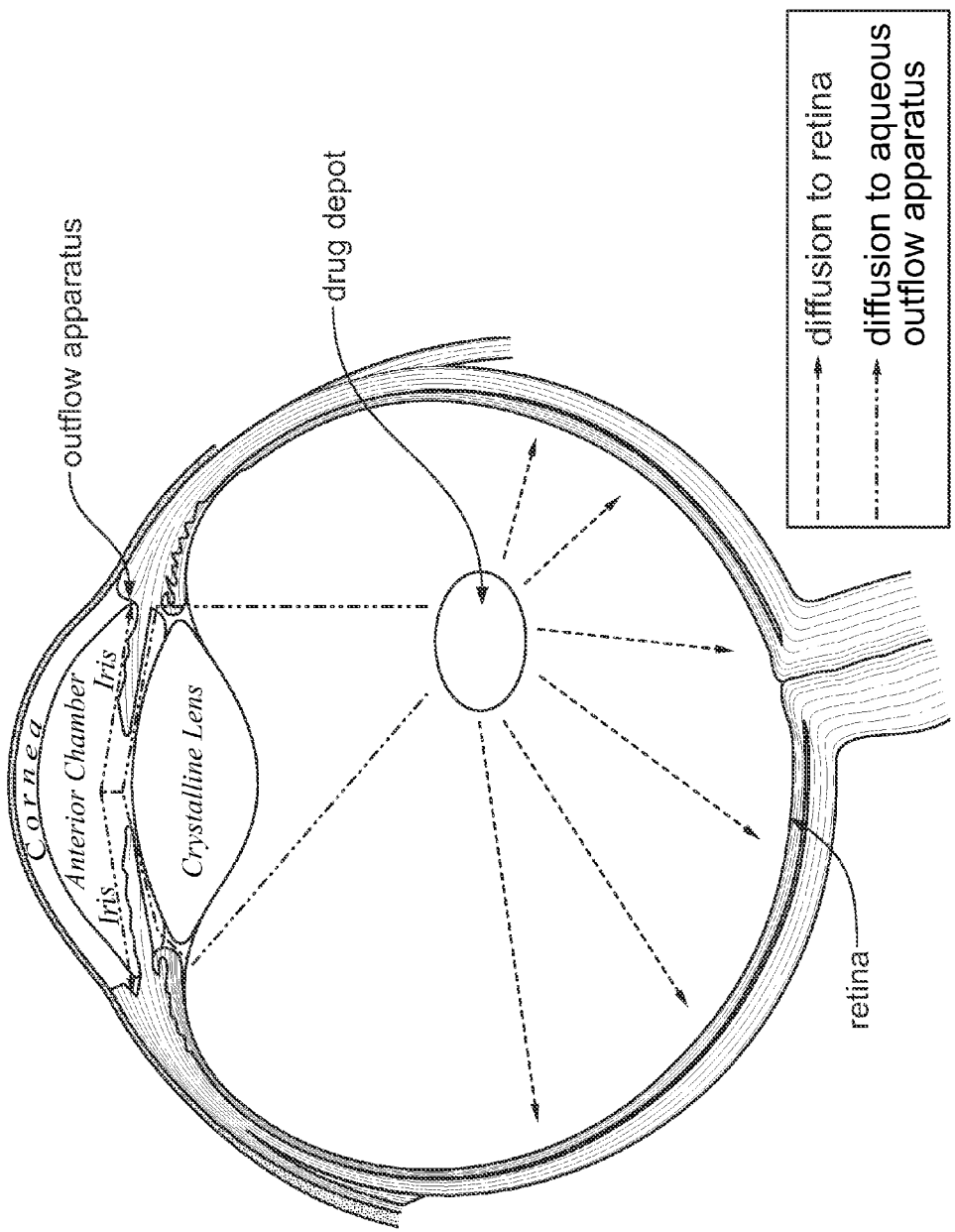
FIG. 1 is a view of the human eye, showing the anterior and posterior segments.

The GDs of the present materials refer to agents that bind or interact with and activate the glucocorticoid receptor. Preferably, the agents bind or interact with the GR to a greater extent than to the mineralcorticoid receptor, even more preferably to an extent at least twice as great, or at least 5 times as great, or at least 10 times as great, or at least 50 times as great, or at least 100 times as great or at least 1000 times as great as the mineralcorticoid receptor. The GDs of the therapeutic component have a greater vitreous humor/aqueous humor concentration ratio and greater vitreal half-life than other steroids identically administered, such as dexamethasone and triamcinolone acetonide.

Posteriorly-directed GDs can be screened, for example, by injecting the potential GD into a rabbit vitreous. The vitreous humor and aqueous humor can be sampled as a function of time, and the amount of the potential GD in the vitreous and aqueous humor can be measured. The vitreous concentration of the potential GD can be plotted as a function of time, and using standard pharmacokinetic techniques, the vitreous half-life for the GD and clearance of the potential GD can be calculated.

Similarly, the aqueous concentration of the GD can be plotted as a function of time, and standard pharmacokinetic techniques can be used to determine the anterior clearance of the potential GD. Agents with desired vitreal half-lives and/or that are selectively present in the vitreous humor rather than the aqueous humor are used in the present materials. For example, agents that have vitreous half-lives greater than about three hours can be selected for the present ophthalmically therapeutic materials.

Pathological Conditions of the Posterior Segment

In part, the present invention is generally drawn to methods for treating the posterior segment of the eye. Preferably, the posterior segment of the eye comprises, without limitation, the uveal tract, vitreous, retina, choroid, optic nerve, and the retinal pigmented epithelium (RPE). The disease or condition related to this invention may comprise any disease or condition that can be prevented or treated by the action of a glucocorticoid, especially a GD, upon a posterior part of the eye. While not intending to limit the scope of this invention in any way, some examples of diseases or conditions that can be prevented or treated by the action of an active drug upon the posterior part of the eye in accordance with the present invention may include maculopathies/retinal degeneration such as macular edema, anterior uveitis, retinal vein occlusion, non-exudative age related macular degeneration, exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infections (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitus, or cytomegalovirus retinitis. Glaucoma can also be considered a posterior ocular condition because the therapeutic goal is to prevent the loss of or reduce the occurrence of loss of vision due to damage to or loss of retinal cells or optic nerve cells (i.e. neuroprotection).

The present materials claimed, and used in the methods claimed, herein include, without limitation, liquid-containing compositions (such as formulations) and polymeric drug delivery systems. The present compositions may be understood to include solutions, suspensions, emulsions, and the like, such as other liquid-containing compositions used in ophthalmic therapies. Polymeric drug delivery systems comprise a polymeric component, and may be understood to include biodegradable implants, nonbiodegradable implants, biodegradable microparticles, such as biodegradable microspheres, and the like. The present drug delivery systems may also be understood to encompass elements in the form of tablets, wafers, rods, sheets, and the like. The polymeric drug delivery systems may be solid, semisolid, or viscoelastic.

As used herein, "periocular" administration refers to delivery of the therapeutic component to a retrobulbar region, a subconjunctival region, a subtenon region, a suprachoroidal region or space, and/or an intrascleral region or space. For example, a posterior directed GD may be associated with water, saline, a polymeric liquid or semisolid carrier, phosphate buffer, or other ophthalmically acceptable liquid carrier. The present liquid-containing compositions are preferably in an injectable form. In other words, the compositions may be intraocularly administered, such as by intravitreal injection, using a syringe and needle or other similar device (e.g., see U.S. Patent Publication No. 2003/0060763), hereby incorporated by reference herein in its entirety, or the compositions can be periocularly administered using an injection device.

Also as used herein the term a "therapeutically effective" amount or concentration means an amount or concentration of a GD or a GD-containing composition sufficient, when applied to the posterior segment of the eye, to improve at least one symptom of a disease, condition or disorder affecting said posterior segment, as compared to an untreated eye.

A "biologically significant amount" means an amount of a GD or other steroid present in the anterior segment of an eye sufficient to cause a statistically significant increase in either or both a) intraocular pressure or b) cataract formation as compared to an untreated eye.

The GD of the present methods and compositions may be present in an amount in the range of about 0.05% or less, or about 0.1% or about 0.2% or about 0.5% to about 5% or about 10% or about 20% or about 30% or more (w/v) of the composition. While the GD may be contained in solution (including, without limitation, a supersaturated solution), in a preferred embodiment the GD is present, at least in part, as crystals or particles in a suspension.

For intravitreally administered compositions, providing relatively high concentrations of the GD (for example, in the form of crystals) may be beneficial in that reduced amounts of the composition may be required to be placed or injected into the posterior segment of the eye in order to provide the same amount or more of the therapeutic component in the posterior segment of the eye relative to other compositions.

In certain embodiments, the material further comprises a GD and an excipient component. The excipient component may be understood to include solubilizing agents, viscosity inducing agents, buffer agents, tonicity agents, preservative agents, and the like.

In some embodiments of the present compositions, a solubilizing agent may be a cyclodextrin. In other words, the present materials may comprise a cyclodextrin component provided in an amount from about 0.1% (w/v) to about 5% (w/v) of the composition. In further embodiments, the cyclodextrin comprises up to about 10% (w/v) of certain cyclodextrins, as discussed herein. In further embodiments, the cyclodextrin comprises up to about 60% (w/v) of certain cyclodextrins, as discussed herein. The excipient component of the present compositions may comprise one or more types of cyclodextrins or cyclodextrin derivatives, such as alpha-cyclodextrins, beta-cyclodextrins, gamma-cyclodextrins, and derivatives thereof. As understood by persons of ordinary skill in the art, cyclodextrin derivatives refer to any substituted or otherwise modified compound that has the characteristic chemical structure of a cyclodextrin sufficiently to function as a cyclodextrin, for example, to enhance the solubility and/or stability of therapeutic agents and/or reduce unwanted side effects of the therapeutic agents and/or to form inclusive complexes with the therapeutic agents.

Viscosity inducing agents of the present materials, include without limitation, polymers that are effective in stabilizing the therapeutic component in the composition. The viscosity-inducing component is present in an effective amount in increasing, advantageously substantially increasing, the viscosity of the composition. Increased viscosities of the present compositions may enhance the ability of the present compositions to maintain the GD, including GD-containing particles, in substantially uniform suspension in the compositions for prolonged periods of time, for example, for at least about one week, without requiring resuspension processing. The relatively high viscosity of certain of the present compositions may also have an additional benefit of at least assisting the compositions to have the ability to have an increased amount or concentration of the GD, as discussed elsewhere herein, for example, while maintaining such GD in substantially uniform suspension for prolonged periods of time.

Direct Intraocular Administration

Preferably, the GDs of the present invention are administered directly to the vitreous chamber of the eye, by means including administration of a solution, suspension, or other means of carrying of crystals or particles of the GD, or as part of an intravitreal implant, by, for example, incision or injection.

The vitreous humor contained in the posterior chamber of the eye is a viscous aqueous substance. Injection of a fluid or suspension of substantially lower viscosity into the posterior segment could therefore result in the presence of two phases or layers of different density within the eye, which in turn can lead to either "pooling" of GD particles or floating of the less dense solution. If the injected or inserted material contains a drug in the form of a solid (for example as crystals, particles or an unsutured implant or reservoir), the solid material will fall to the bottom of the eye and remain there until it dissolves. Additionally, a substantially different refractive index between vitreous and the injected or inserted GD-containing composition may impair vision.

The therapeutic compositions, including the GDs described as part of the present invention, may be suspended in a viscous formulation having a relatively high viscosity, such as one approximating that of the vitreous humor. Such viscous formulation comprises a viscosity-inducing component. The therapeutic agent of the present invention may be administered intravitreally as, without limitation, an aqueous injection, a suspension, an emulsion, a solution, a gel or inserted in a sustained release or extended release implant, either biodegradable or non-biodegradable.

The viscosity-inducing component preferably comprises a polymeric component and/or at least one viscoelastic agent, such as those materials that are useful in ophthalmic surgical procedures.

Examples of useful viscosity-inducing components include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

The molecular weight of the viscosity-inducing components may be in a range up to about 2 million Daltons, such as of about 10,000 Daltons or less to about 2 million Daltons or more. In one particularly useful embodiment, the molecular weight of the viscosity-inducing component is in a range of about 100,000 Daltons or about 200,000 Daltons to about 1 million Daltons or about 1.5 million Daltons.

In one very useful embodiment, a viscosity-inducing component is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons.

In one embodiment, the GDs of the present invention may be comprised in a polymeric hyaluronate component in an amount in a range about 0.01% to about 0.5% (w/v) or more. In a further useful embodiment, the hyaluronate component is present in an amount in a range of about 1% to about 4% (w/v) of the composition. In this latter case, the very high polymer viscosity forms a gel that slows the sedimentation rate of any suspended drug, and prevents pooling of injected GD.

The GD of this aspect of the claimed invention may include any or all salts, prodrugs, conjugates, or precursors of such therapeutically useful GDs, including those specifically identified herein.

In certain embodiments, the compositions of the present invention may comprise more than one therapeutic agent, so long as at least one such therapeutic agent is a GD having one or more of the properties described herein as important to preventing migration of the GD into the anterior segment and/or penetration of the GD into tissue of the posterior segment, which tissue may include, without limitation, retinal tissue. In other words, a therapeutic composition of the present invention, however administered, may include a first therapeutic agent, and one or more additional therapeutic agent, or a combination of therapeutic agents, so long as at least one of such therapeutic agents is a GD. One or more of the therapeutic agents in such compositions may be formed as or present in particles or crystals.

In these aspects of the present invention, the viscosity-inducing component is present in an effective amount to increase, advantageously substantially increase, the viscosity of the composition. Without wishing to limit the invention to any particular theory of operation, it is believed that increasing the viscosity of the compositions to values well in excess of the viscosity of water, for example, at least about 100 cps at a shear rate of 0.1/second, compositions which are highly effective for placement, e.g., injection, into the posterior segment of an eye of a human or animal are obtained. Along with the advantageous placement or injectability of the these GD-containing compositions into the posterior segment, the relatively high viscosity of the present compositions are believed to enhance the ability of such compositions to maintain the therapeutic component (for example, comprising GD-containing particles) in substantially uniform suspension in the compositions for prolonged periods of time, and may aid in the storage stability of the composition.

Advantageously, the compositions of this aspect of the invention may have viscosities of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. In particular embodiments the present compositions not only have the relatively high viscosity noted above but also have the ability or are structured or made up so as to be effectively able to be placed, e.g., injected, into a posterior segment of an eye of a human or animal, preferably through a 27 gauge needle, or even through a 30 gauge needle.

The viscosity inducing components preferably are shear thinning components such that as the viscous formulation is passed through or injected into the posterior segment of an eye, for example, through a narrow aperture, such as 27 gauge needle, under high shear conditions the viscosity of the composition is substantially reduced during such passage. After such passage, the composition regains substantially its pre-injection viscosity so as to maintain any GD-containing particles in suspension in the eye.

Any ophthalmically acceptable viscosity-inducing component may be employed in accordance with the GDs in the present invention. Many such viscosity-inducing components have been proposed and/or used in ophthalmic compositions used on or in the eye. The viscosity-inducing component is present in an amount effective in providing the desired viscosity to the composition. Advantageously, the viscosity-inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the GD-containing composition being produced and/or used and similar factors.

Biocompatible Polymers

In another embodiment of the invention, the therapeutic agents (including at least one GD) may be delivered intraocularly in a composition that comprises, consists essentially of, or consists of, a therapeutic agent comprising a GD and a biocompatible polymer suitable for administration to the posterior segment of an eye. For example, the composition may, without limitation, comprise an intraocular implant or a liquid or semisolid polymer. Some intraocular implants are described in publications including U.S. Pat. Nos. 6,726,918; 6,699,493; 6,369,116; 6,331,313; 5,869,079; 5,824,072; 5,766,242; 5,632,984; and 5,443,505, these and all other publications cited or mentioned herein hereby incorporated by reference herein in their entirety, unless expressly indicated otherwise. These are only examples of particular preferred implants, and others will be available to the person of ordinary skill in the art.

The polymer in combination with the GD-containing therapeutic agent may be understood to be a polymeric component. In some embodiments, the particles may comprise D,L-polylactide (PLA) or latex (carboxylate modified polystyrene beads). In other embodiments the particles may comprise materials other than D,L-polylactide (PLA) or latex (carboxylate modified polystyrene beads). In certain embodiments, the polymer component may comprise a polysaccharide. For example, the polymer component may comprise a mucopolysaccharide. In at least one specific embodiment, the polymer component is hyaluronic acid.

However, in additional embodiments, and regardless of the method of GD administration, the polymeric component may comprise any polymeric material useful in a body of a mammal, whether derived from a natural source or synthetic. Some additional examples of useful polymeric materials for the purposes of this invention include carbohydrate based polymers such as methylcellulose, carboxymethylcellulose, hydroxymethylcellulose hydroxypropylcellulose, hydroxyethylcellulose, ethyl cellulose, dextrin, cyclodextrins, alginate, hyaluronic acid and chitosan, protein based polymers such as gelatin, collagen and glycolproteins, and hydroxy acid polyesters such as bioerodable polylactide-coglycolide (PLGA), polylactic acid (PLA), polyglycolide, polyhydroxybutyric acid, polycaprolactone, polyvalerolactone, polyphosphazene, and polyorthoesters. Polymers can also be crosslinked, blended or used as copolymers in the invention. Other polymer carriers include albumin, polyanhydrides, polyethylene glycols, polyvinyl polyhydroxyalkyl methacrylates, pyrrolidone and polyvinyl alcohol.

Some examples of non-erodible polymers include silicone, polycarbonates, polyvinyl chlorides, polyamides, polysulfones, polyvinyl acetates, polyurethane, ethylvinyl acetate derivatives, acrylic resins, crosslinked polyvinyl alcohol and crosslinked polyvinylpyrrolidone, polystyrene and cellulose acetate derivatives.

These additional polymeric materials may be useful in a composition comprising the therapeutically useful GD agents disclosed herein, or for use in any of the methods, including those involving the intravitreal administration of such methods. For example, and without limitation, PLA or PLGA may be coupled to a GD for use in the present invention, either as particles in suspension or as part of an implant. This insoluble conjugate will slowly erode over time, thereby continuously releasing the GD.

The term “biodegradable polymer” refers to a polymer or polymers which degrade in vivo, and wherein erosion of the polymer or polymers over time occurs concurrent with or subsequent to release of the therapeutic GD agent. The terms “biodegradable” and “bioerodible” are equivalent and are used interchangeably herein. A biodegradable polymer may be a homopolymer, a copolymer, or a polymer comprising more than two different polymeric units.

The term “therapeutically effective amount” as used herein, refers to the level or amount of GD agent needed to treat a condition of the posterior segment, or reduce or prevent ocular injury or damage without causing significant negative or adverse side effects to the anterior segment of the eye.

Formulation Vehicles

Regardless of the mode of administration or form (e.g., in solution, suspension, as a topical, injectable or implantable agent), the GD-containing therapeutic compositions of the present invention will be administered in a pharmaceutically acceptable vehicle component. The therapeutic agent or agents may also be combined with a pharmaceutically acceptable vehicle component in the manufacture of a composition. In other words, a composition, as disclosed herein, may comprise a therapeutic component and an effective amount of a pharmaceutically acceptable vehicle component. In at least one embodiment, the vehicle component is aqueous-based. For example, the composition may comprise water.

In certain embodiments, the GD-containing therapeutic agent is administered in a vehicle component, and may also include an effective amount of at least one of a viscosity inducing component, a resuspension component, a preservative component, a tonicity component and a buffer component. In some embodiments, the compositions disclosed herein include no added preservative component. In other embodiments, a composition may optionally include an added preservative component. In addition, the composition may be included with no resuspension component.

Formulations for topical or intraocular administration of the GD-containing therapeutic agents (including, without limitation, implants or particles containing such agents) will preferably include a major amount of liquid water. Such compositions are preferably formulated in a sterile form, for example, prior to being used in the eye. The above-mentioned buffer component, if present in the intraocular formulations, is present in an amount effective to control the pH of the composition. The formulations may contain, either in addition to, or instead of the buffer component at least one tonicity component in an amount effective to control the tonicity or osmolality of the compositions. Indeed, the same component may serve as both a buffer component and a tonicity component. More preferably, the present compositions include both a buffer component and a tonicity component.

The buffer component and/or tonicity component, if either is present, may be chosen from those that are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, any other suitable ophthalmically acceptably tonicity component and mixtures thereof. Non-ionic tonicity components may comprise polyols derived from sugars, such as xylitol, sorbitol, mannitol, glycerol and the like.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The compositions of, or used in, the present invention may include one or more other components in amounts effective to provide one or more useful properties and/or benefits to the present compositions. For example, although the present compositions may be substantially free of added preservative components, in other embodiments, the present compositions include effective amounts of preservative components, preferably such components that are more compatible with or friendly to the tissue in the posterior segment of the eye into which the composition is placed than benzyl alcohol. Examples of such preservative components include, without limitation, quaternary ammonium preservatives such as benzalkonium chloride ("BAC" or "BAK") and polyoxamer; biguanide preservatives such as polyhexamethylene biguandide (PHMB); methyl and ethyl parabens; hexetidine; chlorite components, such as stabilized chlorine dioxide, metal chlorites and the like; other ophthalmically acceptable preservatives and the like and mixtures thereof. The concentration of the preservative component, if any, in the present compositions is a concentration effective to preserve the composition, and (depending on the nature of the particular preservative used) is often and generally used in a range of about 0.00001% to about 0.05% (w/v) or about 0.1% (w/v) of the composition.

Intravitreal delivery of therapeutic agents can be achieved by injecting a liquid-containing composition into the vitreous, or by placing polymeric drug delivery systems, such as implants and microparticles, such as microspheres, into the vitreous. Examples of biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

Other route of administering the GD-containing therapeutic agents of the present invention to the interior of the eye may include periocular delivery of drugs to a patient. Penetration of drugs directly into the posterior segment of the eye is restricted by the blood-retinal barriers. The blood-retinal barrier is anatomically separated into inner and outer blood barriers. Movement of solutes or drugs into the internal ocular structures from the periocular space is restricted by the retinal pigment epithelium (RPE), the outer blood-retinal barrier. The cells of this structure are joined by zonulae oclludentae intercellular junctions. The RPE is a tight ion transporting barrier that restricts paracellular transport of solutes across the RPE. The permeability of most compounds across the blood-retinal barriers is very low. Lipophilic compounds, however, such as chloramphenical and benzyl penicillin, can penetrate the blood-retinal barrier achieving appreciable concentrations in the vitreous humor after systemic administration. The lipophilicity of the compound correlates with its rate of penetration and is consistent with passive cellular diffusion. The blood retinal barrier, however, is impermeable to polar or charged compounds in the absence of a transport mechanism.

Structure of Exemplary GDs

The GDs of the present invention are compounds that 1) selectively bind to and activate the glucocorticoid receptor (glucocorticoids), 2) have an aqueous solubility less than that of triamcinolone acetonide (21 µg/ml) and/or a lipophilicity (log P) greater than that of triamcinolone acetonide (2.53). Log P is the lipophilicity coefficient, where P is the octonol/water partition coefficient.

According to the present patent application, the basic steroid ring structure is as follows

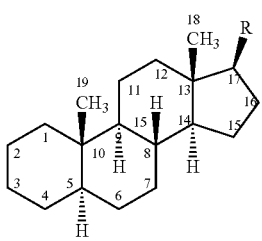

For example, the phosphate salt of the glucocorticoid dexamethosone has the following structure:

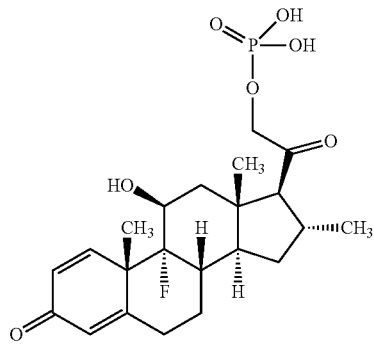

Similarly, the glucocorticoid triamcinolone acetonide has the structure:

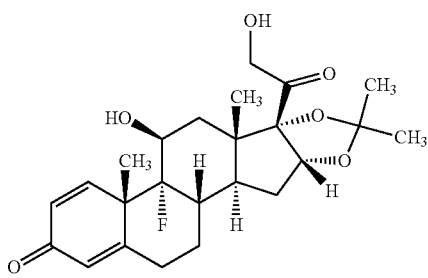

The Glucocorticoid Derivatives (GDs) used in the compositions and methods of the present invention also selectively bind to and activate the glucocorticoid receptor, have an aqueous solubility less than that of triamcinolone acetonide (21 µg/ml) and/or a lipophilicity (log P) greater than that of triamcinolone acetonide (2.53).

In a useful embodiment, the GDs of the present invention comprise an acyl group linked via an ester linkage to a glucocorticoid at the $C_{17}$ position and/or the $C_{21}$ position (if the latter carbon atom is present). Preferably the ester is a monoester linkage. However, in another embodiment the ester is a diester linkage. Useful acyl groups include, without limitation, the acetyl, butyryl, valeryl, propionyl, or furoyl groups. Additional potentially useful groups would include the benzoyl group and/or other substituted or unsubstituted cyclic or aromatic acyl groups. Ideally, the acyl group(s) should have high hydrophobicity; thus alkyl or aromatic acyl groups are particularly preferred in the present application, while those containing polar substituents are less preferred, and in some embodiments of the invention are absent. In certain of the embodiments of the present invention acyl group is linked to the steroid by a thiol ester.

Certain $C_{17}$ and/or $C_{21}$ acyl ester-substituted glucocorticoids are used for treatment of inflammatory and other conditions by routes including, without limitation, such as topical skin or systemic administration. For example, beclomethasone dipropionate is used in the treatment of bronchial asthma and to shrink nasal polyps. It is formulated in a powder form, and is administered by inhalation. It has the following structure:

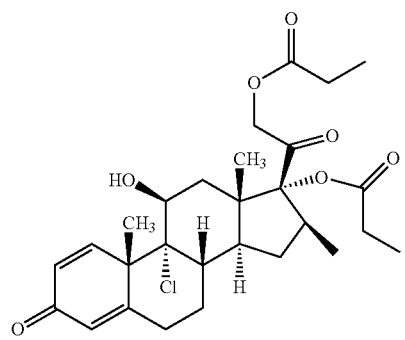

While beclomethasone dipropionate is sometimes called simply "beclomethasone", this is an incorrect use of the chemical nomenclature. Unsubstituted beclomethasone has the following structure:

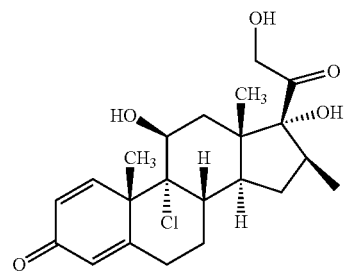

Another compound comprises fluticasone propionate, having the following structure:

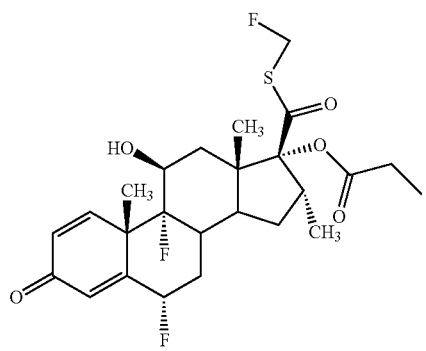

Relative to a "parent" glucocorticoid lacking hydrophobic substitutions(for example, an identical compound lacking the indicated substitutions of a hydrophoblic (preferably acyl ester) group at positions $C_{17}$ and/or $C_{21}$), the addition of such substitutions in accordance with the present invention tends to result in a decreased solubility in aqueous medium and increased lipophilicity coefficient (log P, where P is the octanol/water partition coefficient), and slow the compound's dissolution rate from the crystal to the solubilized phase. These physiochemical attributes experimentally reduce the amount of compound migrating from the posterior segment to the anterior segment, thereby resulting in reduced anterior-segment related side effects. At the same time, these compounds are better able to migrate into the tissues of the posterior segment, such as the retina, the RPE, etc.), thereby selectively being directed to such tissue. When the GDs are administered to the vitreous in crystalline or particulate form, the GDs possess an extended duration of action with intravitreal delivery compared to the parent glucocorticoid.

A non-exclusive list of currently preferred GDs includes, without limitation, dexamethasone 17-acetate, dexamethasone 17, 21-acetate, dexamethasone 21-acetate, clobetasone 17-butyrate, beclomethasone 17, 21-dipropionate, fluticasone 17-propionate, clobetasol 17-propionate, betamethasone 17, 21-dipropionate, alclometasone 17,21-dipropionate, dexamethasone 17,21-dipropionate, dexamethasone 17-propionate, halobetasol 17-propionate, and betamethasone 17-valerate. The use of these compounds for treatment of conditions of the posterior segment of the eye, particularly by ocular administration, such as intravitreal, subconjunctival, subscleral or topical ocular administration will confer a significant therapeutic improvement compared to existing therapies in the treatment of posterior eye diseases such as those listed above, which include, without limitation, dry and wet ARMD, diabetic macular edema, proliferate diabetic retinopathy, uveitis, and ocular tumors.

If desired, buffering agents may be provided in an amount effective to control the pH of the composition. Tonicity agents may be provided in an amount effective to control the tonicity or osmolality of the compositions. Certain of the present compositions include both a buffer component and a tonicity component, which may include one or more sugar alcohols, such as mannitol, or salts, such as sodium chloride, as discussed herein. The buffer component and tonicity component may be chosen from those that are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, any other suitable ophthalmically acceptable tonicity component and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

Preservative agents that may be used in the present materials include benzyl alcohol, benzalkonium chloride, methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

The present compositions can be produced using conventional techniques routinely known by persons of ordinary skill in the art. For example, a GD-containing therapeutic component can be combined with a liquid carrier. The composition can be sterilized. In certain embodiments, such as preservative-free embodiments, the compositions can be sterilized and packaged in single-dose amounts. The compositions may be prepackaged in intraocular dispensers which can be disposed of after a single administration of the unit dose of the compositions.

The present compositions can be prepared using suitable blending/processing techniques, for example, one or more conventional blending techniques. The preparation processing should be chosen to provide the present compositions in forms which are useful for intravitreal or periocular placement or injection into eyes of humans or animals. In one useful embodiment a concentrated therapeutic component dispersion is made by combining the GD-containing therapeutic component with water, and the excipients (other than the viscosity inducing component) to be included in the final composition. The ingredients are mixed to disperse the therapeutic component and then autoclaved. The viscosity inducing component may be purchased sterile or sterilized by conventional processing, for example, by filtering a dilute solution followed by lyophylization to yield a sterile powder. The sterile viscosity inducing component is combined with water to make an aqueous concentrate. The concentrated therapeutic component dispersion is mixed and added as a slurry to the viscosity inducing component concentrate. Water is added in a quantity sufficient (q.s.) to provide the desired composition and the composition is mixed until homogenous.

In one embodiment, a sterile, viscous suspension suitable for administration is made using an GD. A process for producing such a composition may comprise sterile suspension bulk compounding and aseptic filling.

Other embodiments of the present materials are in the form of a polymeric drug delivery system that is capable of providing sustained drug delivery for extended periods of time after a single administration. For example, the present drug delivery systems can release the GD for at least about 1 month, or about 3 months, or about 6 months, or about 1 year, or about 5 years or more. Thus, such embodiments of the present materials may comprise a polymeric component associated with the therapeutic component in the form of a polymeric drug delivery system suitable for administration to a patient by at least one of intravitreal administration and periocular administration.

The polymeric drug delivery system may be in the form of biodegradable polymeric implants, non-biodegradable polymeric implants, biodegradable polymeric microparticles, and combinations thereof. Implants may be in the form of rods, wafers, sheets, filaments, spheres, and the like. Particles are generally smaller than the implants disclosed herein, and may vary in shape. For example, certain embodiments of the present invention utilize substantially spherical particles. These particles may be understood to be microspheres. Other embodiments may utilize randomly configured particles, such as particles that have one or more flat or planar surfaces. The drug delivery system may comprise a population of such particles with a predetermined size distribution. For example, a major portion of the population may comprise particles having a desired diameter measurement.

As discussed herein, the polymeric component of the present drug delivery systems can comprise a polymer selected from the group consisting of biodegradable polymers, non-biodegradable polymers, biodegradable copolymers, non-biodegradable copolymers, and combinations thereof. In certain embodiments, the polymeric component comprises a poly (lactide-co-glycolide) polymer (PLGA). In other embodiments, the polymeric component comprises a polymer selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof. The polymeric component may be associated with the therapeutic component to form an implant selected from the group consisting of solid implants, semisolid implants, and viscoelastic implants.

The GD may be in a particulate or powder form and entrapped by a biodegradable polymer matrix. Usually, GD particles in intraocular implants will have an effective average size measuring less than about 3000 nanometers. However, in other embodiments, the particles may have an average maximum size greater than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers. In addition, when such particles are combined with a polymeric component, the resulting polymeric intraocular particles may be used to provide a desired therapeutic effect.

If formulated as part of an implant or other drug delivery system, the GD of the present systems is preferably from about 1% to 90% by weight of the drug delivery system. More preferably, the GD is from about 20% to about 80% by weight of the system. In a preferred embodiment, the GD comprises about 40% by weight of the system (e.g., 30%-50%). In another embodiment, the GD comprises about 60% by weight of the system.

Suitable polymeric materials or compositions for use in the drug delivery systems include those materials which are compatible, that is biocompatible, with the eye so as to cause no substantial interference with the functioning or physiology of the eye. Such materials preferably include polymers that are at least partially and more preferably substantially completely biodegradable or bioerodible.

In addition to the foregoing, examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present drug delivery systems.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present systems may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Also important to controlling the biodegradation of the polymer and hence the extended release profile of the drug delivery systems is the relative average molecular weight of the polymeric composition employed in the present systems. Different molecular weights of the same or different polymeric compositions may be included in the systems to modulate the release profile. In certain systems, the relative average molecular weight of the polymer will range from about 9 to about 64 kD, usually from about 10 to about 54 kD, and more usually from about 12 to about 45 kD.

In some drug delivery systems, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the system, where a more flexible system or implant is desirable for larger geometries. The % of polylactic acid in the polylactic acid polyglycolic acid (PLGA) copolymer can be 0-100%, preferably about 15-85%, more preferably about 35-65%. In some systems, a 50/50 PLGA copolymer is used.

The biodegradable polymer matrix of the present systems may comprise a mixture of two or more biodegradable polymers. For example, the system may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. It may be understood that the polymeric component of the present systems is associated with the therapeutic component so that the release of the therapeutic component into the eye is by one or more of diffusion, erosion, dissolution, and osmosis. As discussed herein, the matrix of an intraocular drug delivery system may release drug at a rate effective to sustain release of an amount of the GD for more than one week after implantation into an eye. In certain systems, therapeutic amounts of the GD are released for more than about one month, and even for about twelve months or more. For example, the therapeutic component can be released into the eye for a time period from about ninety days to about one year after the system is placed in the interior of an eye.

The release of the GD from the drug delivery systems comprising a biodegradable polymer matrix may include an initial burst of release followed by a gradual increase in the amount of the GD released, or the release may include an initial delay in release of the GD followed by an increase in release. When the system is substantially completely degraded, the percent of the GD that has been released is about one hundred.

It may be desirable to provide a relatively constant rate of release of the therapeutic agent from the drug delivery system over the life of the system. For example, it may be desirable for the GD to be released in amounts from about 0.01 μg to about 2 μg per day for the life of the system. However, the release rate may change to either increase or decrease depending on the formulation of the biodegradable polymer matrix. In addition, the release profile of the GD may include one or more linear portions and/or one or more non-linear portions. Preferably, the release rate is greater than zero once the system has begun to degrade or erode.

The drug delivery systems, such as the intraocular implants, may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the GD falls within a narrow window. In addition, the therapeutic component, including the therapeutic agent(s) described herein, may be distributed in a non-homogenous pattern in the matrix. For example, the drug delivery system may include a portion that has a greater concentration of the GD relative to a second portion of the system.

The polymeric implants disclosed herein may have a size of between about 5 μm and about 2 mm, or between about 10 μm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. However, larger implants may also be formed and further processed before administration to an eye. In addition, larger implants may be desirable where relatively greater amounts of the GD are provided in the implant. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Drug delivery systems can be prepared where the center may be of one material and the surface may have one or more layers of the same or a different composition, where the layers may be cross-linked, or of a different molecular weight, different density or porosity, or the like. For example, where it is desirable to quickly release an initial bolus of GD, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The drug delivery systems may be of any geometry including fibers, sheets, films, microspheres, spheres, circular discs, plaques and the like. The upper limit for the system size will be determined by factors such as toleration for the system, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 μm to 4 mm in diameter, with comparable volumes for other shaped particles.

The size and form of the system can also be used to control the rate of release, period of treatment, and drug concentration at the site of implantation. For example, larger implants will deliver a proportionately larger dose, but depending on the surface to mass ratio, may have a slower release rate. The particular size and geometry of the system are chosen to suit the site of implantation.

The proportions of GD-containing therapeutic agent, polymer, and any other modifiers may be empirically determined by formulating several implants, for example, with varying proportions of such ingredients. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as by spectrophotometry, HPLC, mass spectroscopy, etc. until the absorbance becomes constant or until greater than 90% of the drug has been released.

In addition to the GD-containing therapeutic component, and similar to the compositions described herein, the polymeric drug delivery systems disclosed herein may include an excipient component. The excipient component may be understood to include solubilizing agents, viscosity inducing agents, buffer agents, tonicity agents, preservative agents, and the like.

Additionally, release modulators such as those described in U.S. Pat. No. 5,869,079 may be included in the drug delivery systems. The amount of release modulator employed will be dependent on the desired release profile, the activity of the modulator, and on the release profile of the therapeutic agent in the absence of modulator. Electrolytes such as sodium chloride and potassium chloride may also be included in the systems. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Various techniques may be employed to produce such drug delivery systems. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the drug delivery systems, and typically yield elements with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

In certain embodiments of the present invention, a method of producing a sustained-release intraocular drug delivery system, comprises combining an GD and a polymeric material to form a drug delivery system suitable for placement in an eye of an individual. The resulting drug delivery system is effective in releasing the GD into the eye for extended periods of time. The method may comprise a step of extruding a particulate mixture of the GD and the polymeric material to form an extruded composition, such as a filament, sheet, and the like.

When polymeric particles are desired, the method may comprise forming the extruded composition into a population of polymeric particles or a population of implants, as described herein. Such methods may include one or more steps of cutting the extruded composition, milling the extruded composition, and the like.

As discussed herein, the polymeric material may comprise a biodegradable polymer, a non-biodegradable polymer, or a combination thereof. Examples of polymers include each and every one of the polymers and agents identified above.

Embodiments of the present invention also relate to compositions comprising the present drug delivery systems. For example, and in one embodiment, a composition may comprise the present drug delivery system and an ophthalmically acceptable carrier component. Such a carrier component may be an aqueous composition, for example saline or a phosphate buffered liquid.

Another embodiment relates to a method of producing an ophthalmically therapeutic material which comprises an GD. In a broad aspect, the method comprises the steps of selecting an GD and combining the selected GD with a liquid carrier component or a polymeric component to form a material suitable for administration to an eye. Or stated differently, a method of producing the present materials may comprise a step of selecting GDs having a low aqueous humor/vitreous humor concentration ratio and long intravitreal half-life.

The method may further comprise one or more of the following steps, which will typically be used to select the GD: administering an GD to an eye of a subject and determining the concentration of the GD in at least one of the vitreous humor and aqueous humor as a function of time; and administering a GD to an eye of a subject and determining at least one of the vitreous half-life and clearance of the GD from the posterior chamber of the eye.

The material formed in the method may be a liquid-containing composition, a biodegradable polymeric implant, a non-biodegradable polymeric implant, polymeric microparticles, or combinations thereof. As discussed herein, the material may be in the form of solid implants, semisolid implants, and viscoelastic implants. In certain embodiments, the GD is combined with a polymeric component to form a mixture, and the method further comprises extruding the mixture.

Additional embodiments of the present invention related to methods of improving or maintaining vision of an eye of a patient. In general, the methods comprise a step of administering the present ophthalmically therapeutic material to an eye of an individual in need thereof. Administration, such as intravitreal or periocular (or less preferably, topical) administration of the present materials can be effective in treating posterior ocular conditions without significantly affecting the anterior chamber. The present materials may be particularly useful in treating inflammation and edema of the retina. Administration of the present materials are effective in delivering the GD to one or more posterior structures of the eye including the uveal tract, the vitreous, the retina, the choroid, the retinal pigment epithelium.

When a syringe apparatus is used to administer the present materials, the apparatus can include an appropriately sized needle, for example, a 27-gauge needle or a 30-gauge needle. Such apparatus can be effectively used to inject the materials into the posterior segment or a periocular region of an eye of a human or animal. The needles may be sufficiently small to provide an opening that self seals after removal of the needle.

The present methods may comprise a single injection into the posterior segment of an eye or may involve repeated injections, for example over periods of time ranging from about one week or about 1 month or about 3 months to about 6 months or about 1 year or longer.

The present materials are preferably administered to patients in a sterile form. For example, the present materials may be sterile when stored. Any routine suitable method of sterilization may be employed to sterilize the materials. For example, the present materials may be sterilized using radiation. Preferably, the sterilization method does not reduce the activity or biological or therapeutic activity of the therapeutic agents of the present systems.

The materials can be sterilized by gamma irradiation. As an example, the drug delivery systems can be sterilized by 2.5 to 4.0 mrad of gamma irradiation. The drug delivery systems can be terminally sterilized in their final primary packaging system including administration device e.g. syringe applicator. Alternatively, the drug delivery systems can be sterilized alone and then aseptically packaged into an applicator system. In this case the applicator system can be sterilized by gamma irradiation, ethylene oxide (ETO), heat or other means. The drug delivery systems can be sterilized by gamma irradiation at low temperatures to improve stability or blanketed with argon, nitrogen or other means to remove oxygen. Beta irradiation or e-beam may also be used to sterilize the implants as well as UV irradiation. The dose of irradiation from any source can be lowered depending on the initial bioburden of the drug delivery systems such that it may be much less than 2.5 to 4.0 mrad. The drug delivery systems may be manufactured under aseptic conditions from sterile starting components. The starting components may be sterilized by heat, irradiation (gamma, beta, UV), ETO or sterile filtration. Semi-solid polymers or solutions of polymers may be sterilized prior to drug delivery system fabrication and GD incorporation by sterile filtration of heat. The sterilized polymers can then be used to aseptically produce sterile drug delivery systems.

In another aspect of the invention, kits for treating an ocular condition of the eye are provided, comprising: a) a container, such as a syringe or other applicator, comprising an GD as herein described; and b) instructions for use. Instructions may include steps of how to handle the material, how to insert the material into an ocular region, and what to expect from using the material. The container may contain a single dose of the GD.

EXAMPLES

Example 1

Recombinant vascular endothelial growth factor (VEGF) was obtained from a supplier (R&D Systems). Female Dutch Belt rabbits were anaesthetized with isoflurane inhalation and topical 0.5% proparacaine hydrochloride, and intravitreal injection of one eye with 500 ng VEGF in sterile phosphate buffered saline (PBS) containing 0.1% bovine serum albumin was performed using a 28 guage ½ inch needle. The other eye is given the same volume of the vehicle, without the VEGF.

The extent of VEGF-induced BRB and BAB breakdown of the blood retinal barrier and the blood aqueous barrier was measured by scanning ocular fluorophotemetry (Fluorotron Master, Ocumetrics Inc.); at various times following intravitreal injection. In this model a fluorescent label is administered intravenously, following by determination of the amount of fluorescenin in the anterior and posterior segment and an indication of iridial and retinal leakage, respectively.

Under normal conditions the blood retinal and blood aqueous barrier prevents solutes in the blood from infiltrating the vitreous (and to a somewhat lesser but very significant extent, the aqueous). By contrast, in the presence of retinal disease such as macular degeneration, retinopathy, macular edema, retinal neovascularization etc., there is leakage of blood into retinal tissue, and the fluorescent tracer will be visible in the vitreous and aqueous of the eye. VEGF injection mimics this pathological condition.

Figure 2:
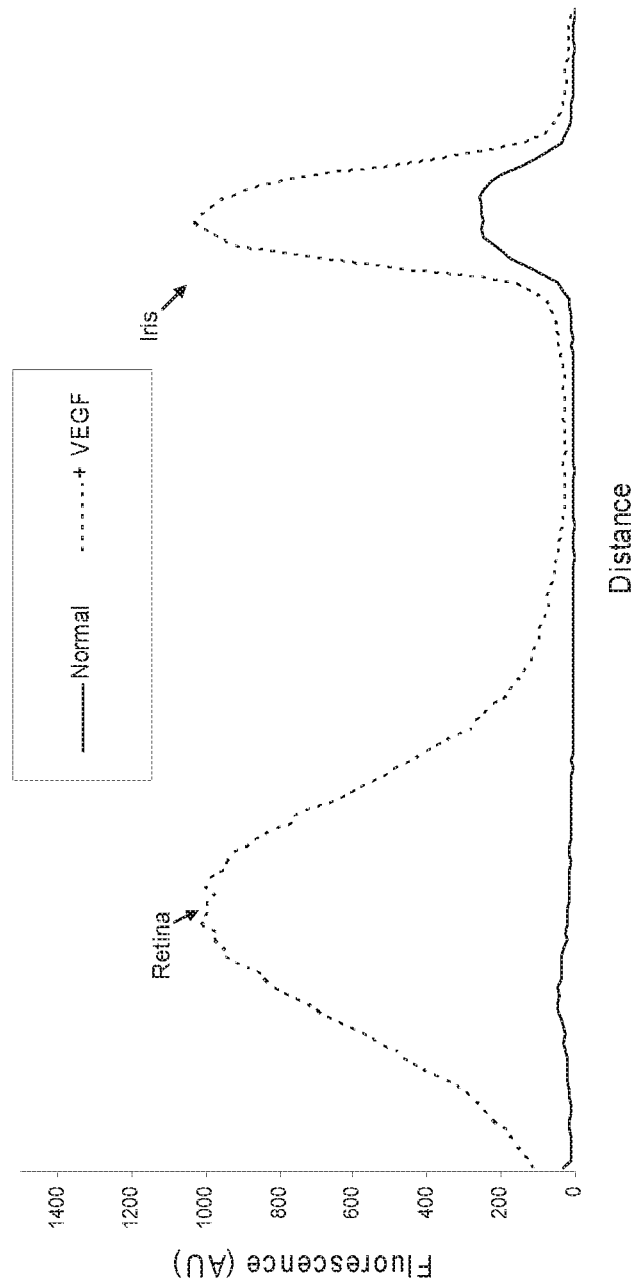
FIG. 2 shows scanning ocular fluorophotemetry traces of fluorescein leakage (arbitrary fluorescence units) from rabbit retina and iris in a single eye two days after intravitreal VEGF injection in that eye, and 50 minutes after intravenous fluorescein injection (12 mg/kg).

FIG. 2 shows representative traces of fluorescein leakage (arbitrary fluorescence units) from rabbit retina and iris from a single eye two days (48 hours) after intravitreal VEGF injection. Sodium fluorescein in 1 ml saline was injected via the marginal ear vein at a concentration of 50 mg/kg, and ocular fluorescein levels in the vitreoretinal chamber and the anterior chamber was determined 50 minutes later.

Compared to normal untreated rabbit eyes, VEGF caused an approximately 18-fold increase in fluorescein contained in the vitreous, and an approximately 6-fold increase in fluorescein contained in the aqueous, which reflects breakdown in the blood retinal barrier (BRB) causing retinal leakage, and the blood aqueous barrier (BAB) iris leakage), respectively.

Both of these responses were completely blocked by the corticosteroids dexamethasone, triamcinolone and beclomethasone, when these corticosteroids were either administered systemically or intravitreally. See infra and Edelman et al., Exp. Eye Res. 80:249-258 (2005), incorporated by reference herein. Thus, when, after steroid treatment, both the anterior and posterior chambers are free of fluorescein leakage following VEGF challenge, this indicates that the steroid is able to infiltrate both chambers effectively.

Five corticosteroids (dexamethasone, triamcinolone, fluticasone propionate, beclomethasone dipropionate and beclomethasone) were purchased from Sigma-Aldrich Co. and evaluated in this model system. In combination these compounds define a solubility range of nearly three log units (1000 fold) from the most water soluble to the least water soluble, and a range of lipophilicity coefficients, log P, from 1.95 to 4.4.

Ten milligrams of each compound is added to 1 ml of sterile phosphate-buffered saline (PBS; ph 7.4). At day 0, 100 ml of a 10 mg/ml suspension of each steroid is injected into the vitreous of a rabbit eye. The PBS vehicle is injected into the other eye. VEGF is then injected at a pre-determined time (one month) thereafter, and BRB and BAB breakdown were measured by scanning ocular fluorophotometry 48 hrs later as described in Edelman et al., Exp. Eye Res. 80:249-258 (2005), hereby incorporated by reference herein in its entirety.

| Compound | Water Solubility | Lipophicity (log P) |
|---|---|---|
| Dexamethasone (Sigma cat. # D1756) | 100 mg/ml | 1.95 |
| Triamcinolone acetonide (Sigma cat. # T6501) | 21.0 mg/ml | 2.53 |
| Fluticasone propionate (Sigma cat. # F9428) | 0.14 mg/ml | 4.20 |
| Beclomethasone dipropionate (Sigma cat. # B3022) | 0.13 mg/ml | 4.40 |

Figure 3:
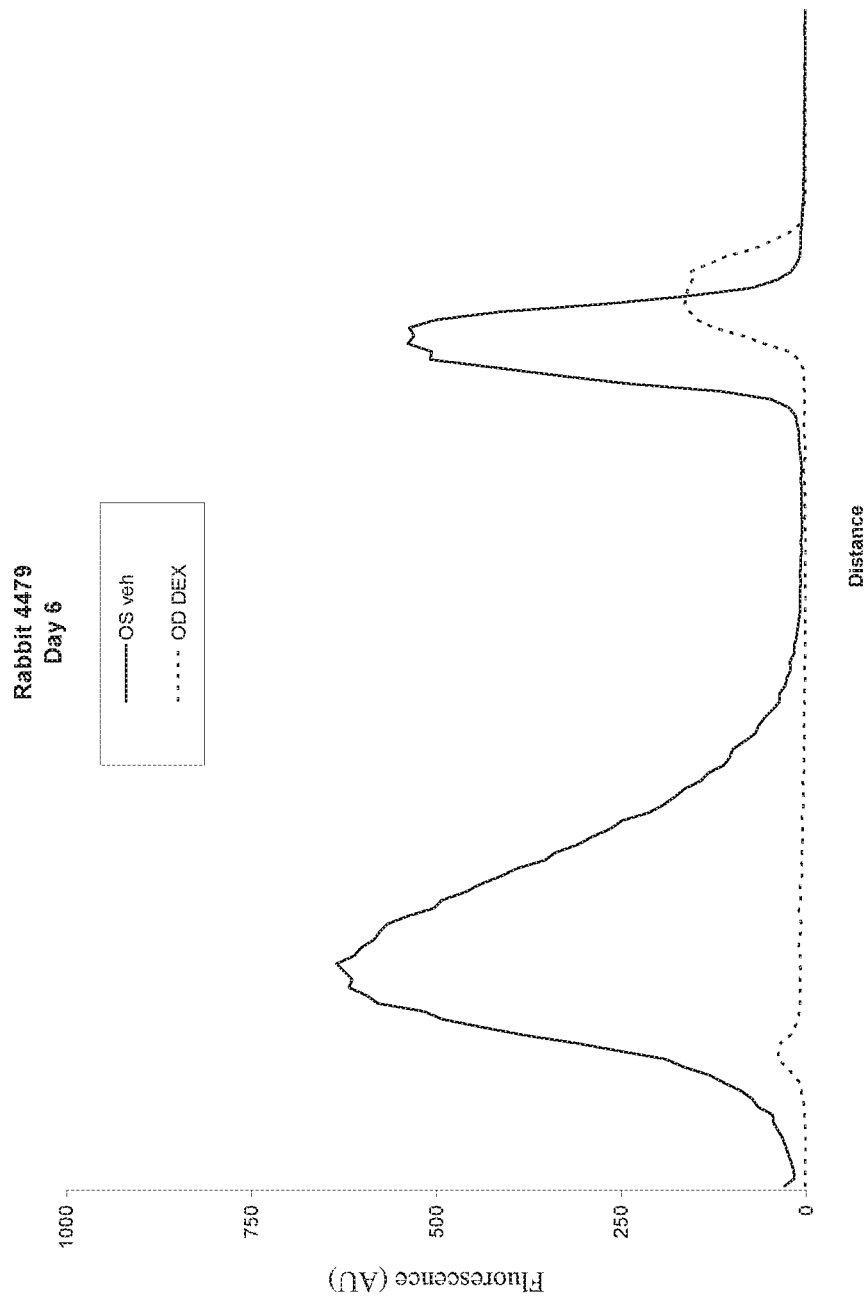
FIG. 3 shows scanning ocular fluorophotemetry traces of fluorescein leakage (arbitrary fluorescence units) from rabbit retina and iris in a single eye treated with 1 mg (100 µL) crystalline dexamethasone suspended in PBS, two days after intravitreal VEGF injection in that eye, and 50 minutes after intravenous fluorescein injection (12 mg/kg). The results indicate that intravitreally-administered dexamethasone is present in both posterior and anterior segments to inhibit BRB and BAB breakdown, respectively.

As can be seen, of the compounds tested dexamethasone (DEX) had the highest water solubility (100 mg/ml) and lowest lipophilicity (log P=1.95) of the five compounds tested. After intravitreal injection of 1 mg crystalline dexamethasone suspended in 100 μL PBS, dexamethasone completely inhibited VEGF-induced leakage of intravenous fluorescein into both the posterior segment and the anterior segment, indicating that intravitreally administered dexamethasone is present in both posterior and anterior segments to inhibit BRB and BAB breakdown, respectively (FIG. 3). Since the BAB is normally relatively leaky compared to the BRB (see FIG. 1), there is some residual fluorescence observed in the anterior chamber of rabbit eyes treated with dexamethasone.

This result indicated that intravitreally administered dexamethasone readily diffuses from the crystal depot within the vitreous in both directions: in the posterior direction to the retinal vasculature and in the anterior direction to the iris. These characteristics result in pharmacologically active levels within both tissues.

Figure 4:
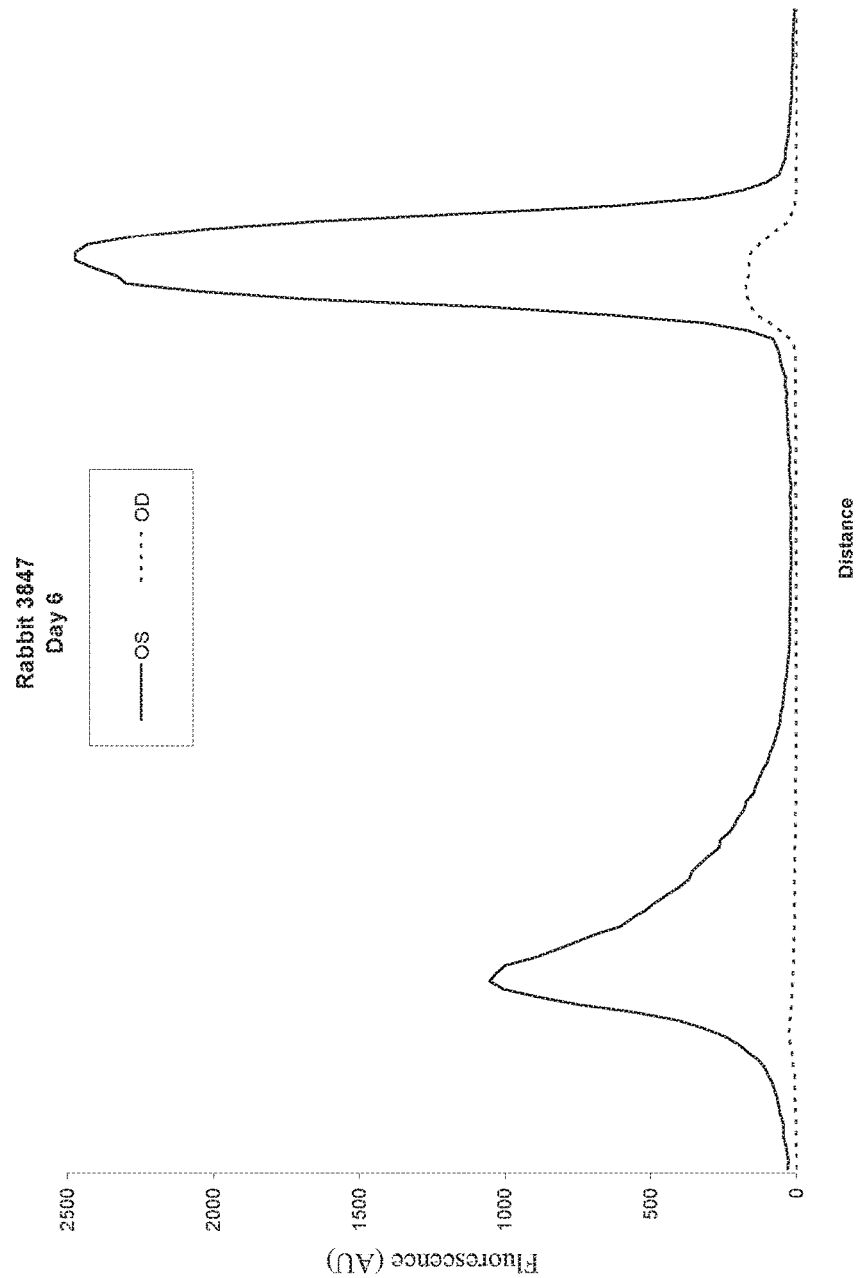
FIG. 4 shows scanning ocular fluorophotemetry traces of fluorescein leakage (arbitrary fluorescence units) from rabbit retina and iris in a single eye treated with 1 mg of triamcinolone acetonide contained in 100 µL of an aqueous suspension and injected into the vitreous under the same conditions described for FIG. 3. This also completely inhibited VEGF-stimulated BRB and BAB breakdown.

Similar to the result with dexamethasone, 1 mg of triamcinolone acetonide contained in 100 μL of an aqueous suspension and injected into the vitreous also completely inhibited VEGF-stimulated BRB and BAB breakdown (FIG. 4).

Figure 5:
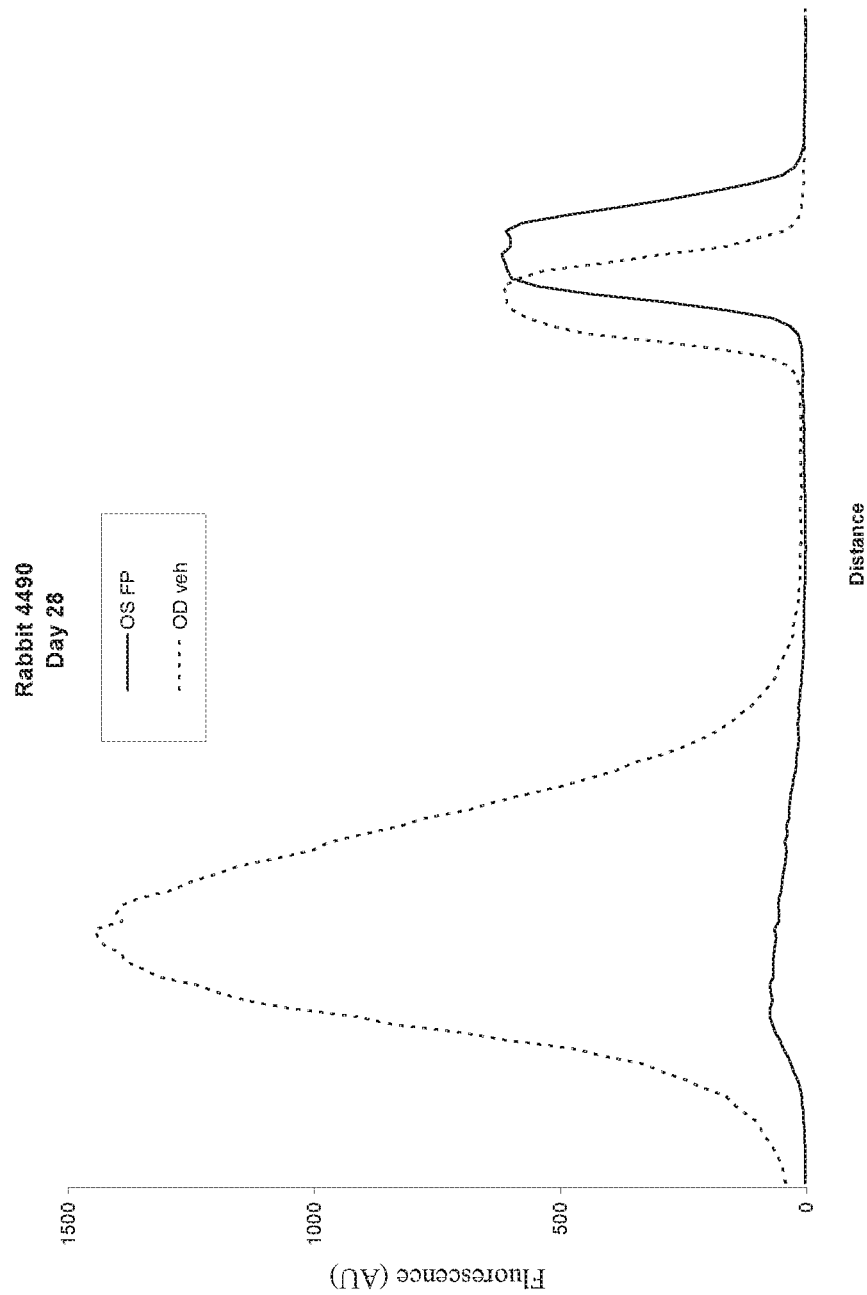
FIG. 5 shows scanning ocular fluorophotemetry traces of fluorescein leakage (arbitrary fluorescence units) from rabbit retina and iris in a single eye treated with 100 µl (1 mg) of an aqueous suspension of beclomethasone was injected into the vitreous of a rabbit eye, followed by VEGF as described above. As with dexamethasone and triamcinolone, beclomethasone inhibited the VEGF-induced BRB and BAB breakdown.

As a final example of the effect of unsubstituted glucocorticoids, 100 μl of a 10 mg/ml suspension of aqueous beclomethasone was injected into the vitreous of a rabbit eye, followed by VEGF as described above. As with dexamethasone and triamcinolone, beclomethasone inhibited the VEGF-induced breakdown of the BRB and the BAB (FIG. 5).

Figure 6:
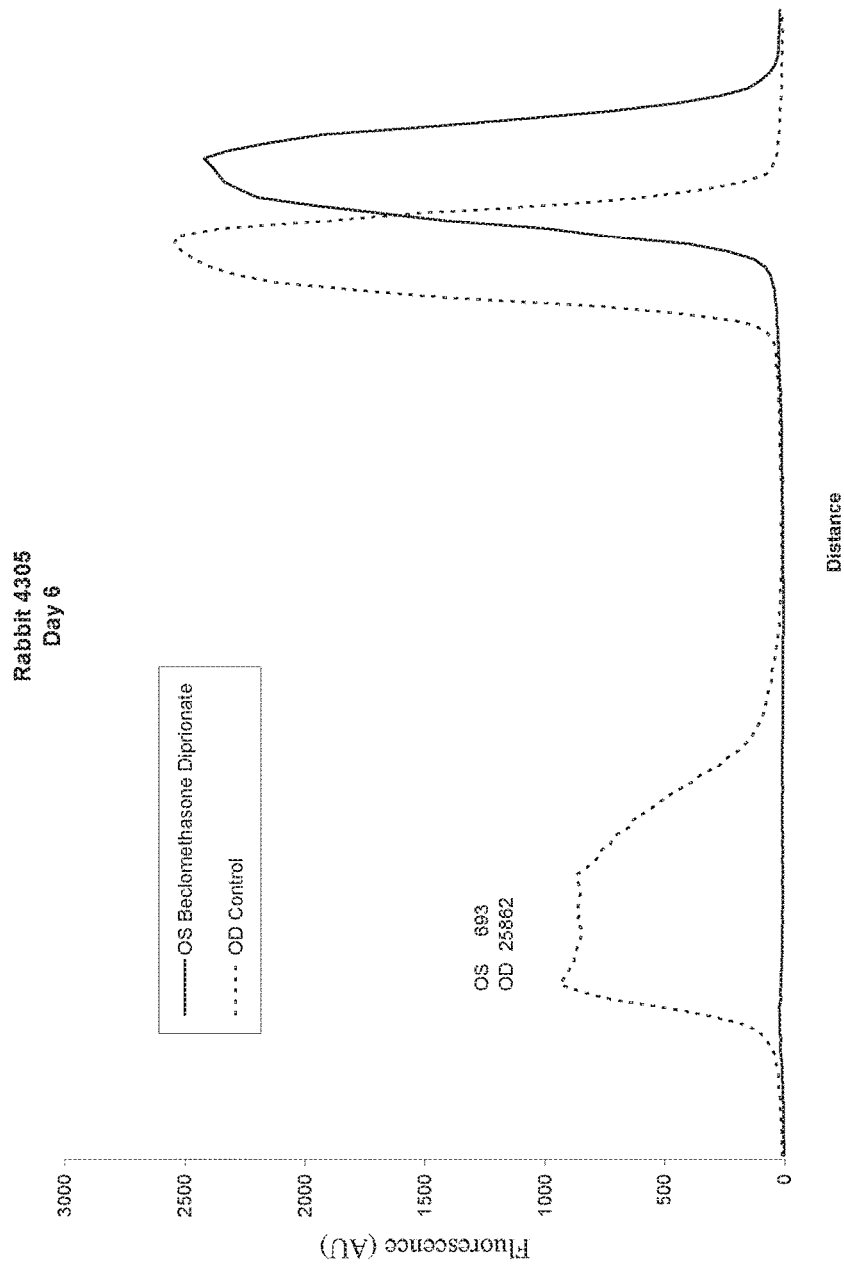
FIG. 6 shows scanning ocular fluorophotemetry traces of fluorescein leakage in rabbit eye injected with VEGF, and indicates that 1 mg (100 µl) fluticasone propionate followed by intravitreal administration of VEGF, completely blocks BRB breakdown but has no effect on BAB breakdown.

In contrast, intravitreal injection of rabbit eye with 100 μl of a 10 mg/ml suspension of fluticasone propionate (water solubility 0.14 mg/ml; log P=4.2), followed by intravitreal administration of VEGF, completely blocked BRB breakdown but had no effect on BAB breakdown (FIG. 6). This result indicates that the intravitreally placed drug is able to diffuse in therapeutically effective concentrations from the vitreous posteriorly to the retina, but is unable to diffuse from the posterior chamber to the anterior chamber in such concentration.

Figure 7:
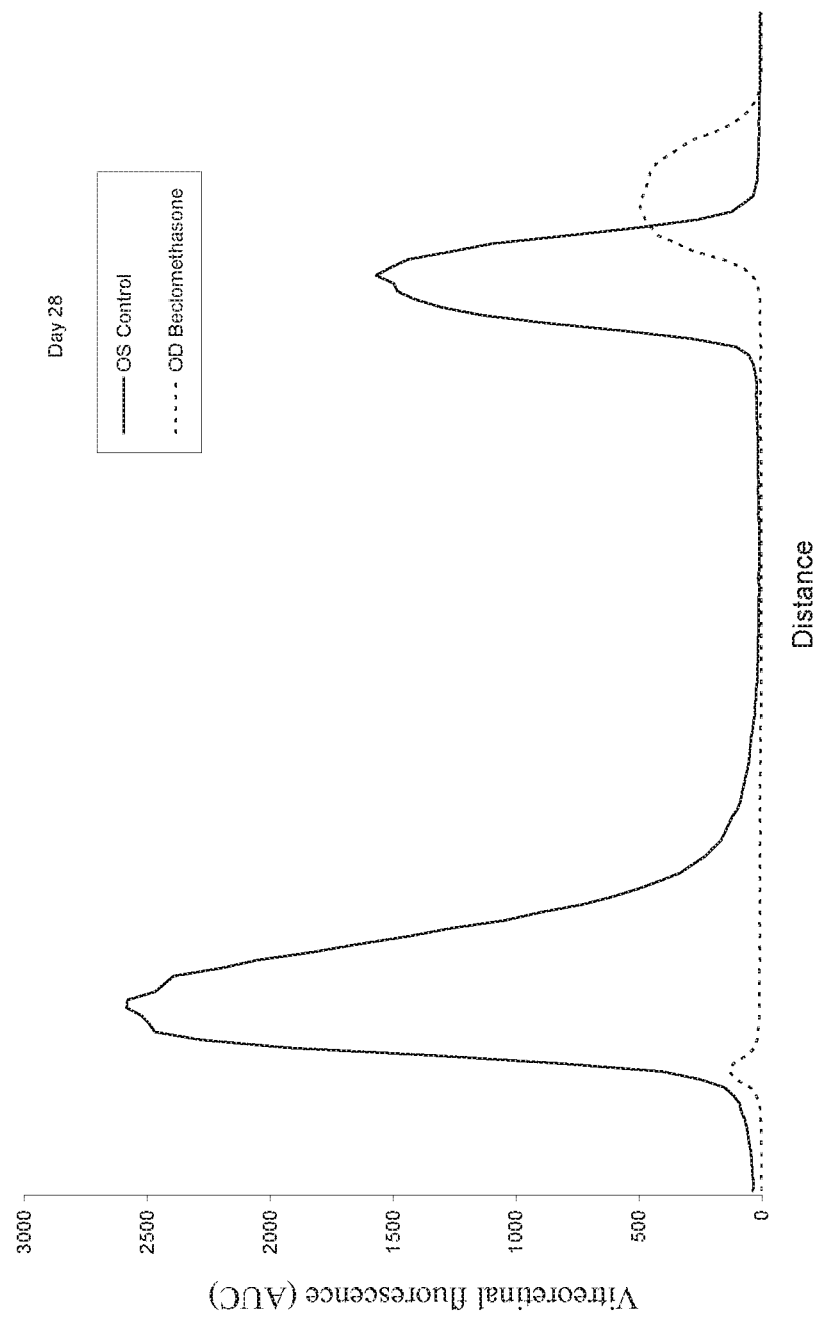
FIG. 7 shows scanning ocular fluorophotemetry traces of fluorescein leakage in rabbit eye injected with VEGF, and indicates that 1 mg (100 µl) beclomethasone 17,21-dipropionate followed by intravitreal administration of VEGF, completely blocks BRB breakdown but has no effect on BAB breakdown.

Similarly, another sparingly water soluble compound, beclomethasone 17,21-dipropionate (0.13 mg/ml; log P=4.4), appears to completely block VEGF-induced BRB breakdown, but has no effect on BAB breakdown (FIG. 7). Moreover, 100 μl of 10 mg/ml intravitreal beclomethasone 17,21-dipropionate completely inhibited VEGF-mediated responses for greater than 3 months.

These results indicate that GDs that possessing one or more hydrophobic $C_{17}$ and/or $C_{21}$ substitution (in this case, an acyl monoester functional group, such as propionate) have reduced water solubility, increased lipophilicity, and are superior pharmacophores for intravitreal delivery to treat ocular diseases that largely or solely involve the posterior segment or have little or no anterior chamber components. Intravitreal administration of these compounds therefore display few, reduced, or abrogated anterior segment side effects such as cataracts, high IOP, and steroid inducted glaucoma. Specific examples of these compounds include dexamethasone 17-acetate, dexamethasone 17, 21-acetate, dexamethasone 21-acetate, clobetasone 17-butyrate, beclomethasone 17, 21-dipropionate, fluticasone 17-propionate, clobetasol 17-propionate, betamethasone 17, 21-dipropionate, alclometasone 17,21-dipropionate, dexamethasone 17,21-dipropionate, dexamethasone 17-propionate, halobetasol 17-propionate, betamethasone 17-valerate. These compounds will be a significant improvement compared to existing therapies in the treatment of posterior eye diseases including, without limitation, dry and wet ARMD, diabetic macular edema, proliferate diabetic retinopathy, uveitis, and ocular tumors.

Example 2

GD Implant

Biodegradable drug delivery systems can be made by combining a GD with a biodegradable polymer composition in a stainless steel mortar. The combination is mixed via a Turbula shaker set at 96 RPM for 15 minutes. The powder blend is scraped off the wall of the mortar and then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods have dimensions of about 2 mm long×0.72 mm diameter. The rod implants weigh between about 900 μg and 1100 μg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 μg and 1100 μg.

In-vitro release testing can be performed on each lot of implant (rod or wafer). Each implant may be placed into a 24 mL screw cap vial with 10 mL of Phosphate Buffered Saline solution at 37° C. and 1 mL aliquots are removed and replaced with equal volume of fresh medium on day 1, 4, 7, 14, 28, and every two weeks thereafter.

Drug assays may be performed by HPLC, which consists of a Waters 2690 Separation Module (or 2696), and a Waters 2996 Photodiode Array Detector. An Ultrasphere, C-18 (2), 5 □m; 4.6×150 mm column heated at 30° C. can be used for separation and the detector can be set at 264 nm. The mobile phase can be (10:90) MeOH-buffered mobile phase with a flow rate of 1 mL/min and a total run time of 12 min per sample. The buffered mobile phase may comprise (68:0.75:0.25:31) 13 mM 1-Heptane Sulfonic Acid, sodium salt—glacial acetic acid—triethylamine—Methanol. The release rates can be determined by calculating the amount of drug being released in a given volume of medium over time in □g/day.

The polymers chosen for the implants can be obtained from Boehringer Ingelheim or Purac America, for example. Examples of polymers include: RG502, RG752, R202H, R203 and R206, and Purac PDLG (50/50). RG502 is (50:50) poly(D,L-lactide-co-glycolide), RG752 is (75:25) poly(D, L-lactide-co-glycolide), R202H is 100% poly(D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 daltons, respectively.

Example 3

Manufacture of Double Extrusion GD Implant

Double extrusion methods may also be used for the manufacture of GD implants. Such implants can be made as follows, and as set forth in as set forth in U.S. patent application Ser. No. 10/918,597, hereby incorporated by reference herein.

Thirty grams of RG502 were milled using the Jet-Mill (a vibratory feeder) at milling pressures of 60 psi, 80 psi and 80 psi for the pusher nozzle, grinding nozzle, and grinding nozzle, respectively. Next, 60 grams of RG502H were milled using the Jet-Mill at milling pressure of 20 psi, 40 psi and 40 psi for the pusher nozzle, grinding nozzle, and grinding nozzle, respectively. The mean particle size of both RG502 and RG502H is measured using a TSI 3225 Aerosizer DSP Particle Size Analyzer. Both milled polymers have a mean particle size of no greater than 20 um.

(b) Blending of GD and PLGA 48 grams of beclamethasone diprionate ("DP"), 24 grams of milled RG502H and 8 grams of milled RG502 are blended using the Turbula Shaker set at 96 RPM for 60 minutes. For the first extrusion, all 80 grams of the blended DP/RG502H/RG502 mixture are added to the hopper of a Haake Twin Screw Extruder. The Haake extruder is then turned on and the following parameters are set:
Barrel Temperature: 105 degrees C.
Nozzle Temperature: 102 degrees C.
Screw Speed: 120 RPM
Feed Rate Setting: 250
Guide Plate Temperature: 50-55 degrees C.
Circulating water bath: 10 degrees C.

The extruded filament is collected. The first filament begins extruding about 15-25 minutes after the addition of the powder blend. The filaments extruded in the first five minutes at these settings are discarded. The remaining filaments are collected until exhaustion of extrudates; this normally takes from 3 to 5 hours.

The resulting filaments are pelletized using the Turbula Shaker and one 19 mm stainless steel ball set at 96 RPM for 5 minutes.

In the second extrusion all the pellets from the last step are added into the same hopper and the Haake extruder turned on.
The extruder is set as follows:
Barrel Temperature: 107° C.
Nozzle temperature: 90° C.
Screw speed: 100 RPM
Guide Plate Temperature: 60-65° C.
Circulation water bath: 10° C.

All extruded filaments are collected until exhaustion of extrudates. This normally takes about 3 hours. The bulk filaments are cut to an appropriate length to give the desired dosage strengths, for example 350 µg and 700 µg. The single and double extruded implants have the characteristics shown by the following Tables 1 and 2, respectively.

TABLE 1

| In Process Controls for the First Extrusion | | | | | |
|---|---|---|---|---|---|
| | | | Batch Number | | |
| | | | 03J001 | 03H004 | 03M001 |
| | | | | Batch size | |
| Parameter | Specifications | | 80 g | 80 g | 80 g |
| Filament density | 0.85 to 1.14 g/cm³ | | 1.03 | 1.01 | 1.04 |
| Uniformity | 85.0 to 115.0%[1] | | 99.3 | 100.5 | 98.7 |
| Potency | 97.0 to 103.0% label strength | | 100.1 | 100.0 | 99.8 |
| Degradation products | ≤1.5% total | | 0.2 | 0.2 | 0.2 |
| | ≤0.75% acid | | ND | ND | ND |
| | ≤0.75% ketone | | ≤0.08 | ≤0.10 | ≤0.13 |
| | ≤0.75% aldehyde | | ≤0.15 | ≤0.10 | ≤0.12 |

[1]Percentage of target weight

TABLE 2

| In Process Controls for the second extrusion | | | | |
|---|---|---|---|---|
| | | Batch number | | |
| | | 03J001 | 03H004 | 03M001 |
| | | Batch size | | |
| Parameter | Specifications | 80 g | 80 g | 80 g |
| Appearance | White to off white | pass | pass | pass |
| Filament density | 1.10 to 1.30 g/cm³ | 1.18 | 1.13 | 1.19 |
| Diameter | ≤80% within 0.0175 to 0.0185 inch | 100 | 100 | 100 |
| Fracture force | ≤2 g | 9.88 | 9.39 | 9.52 |
| Fracture energy | ≤0.9 µJ | 5.88 | 4.54 | 4.64 |
| Moisture | ≥1.0% | 0.4 | 0.4 | 0.4 |
| Foreign particulate | No visible foreign materials | Pass | Pass | Pass |
| Insoluble mater (for information only) | Particle count | | | |
| | Diameter ≤ 10 µm | 17 | 26 | 2.6 |
| | Diameter ≤ 25 µm | 0.5 | 1 | 0 |
| GD identity | Positive for GD | positive | positive | positive |
| Potency | 95.0 to 105.0% label strength | 98.5 | 101.2 | 99.9 |
| Degradation products | ≤2% total | 1.1 | 0.6 | 1.0 |
| | ≤0.5% acid | ND | ND | ND |
| | ≤1.0% ketone | 0.4 | 0.2 | 0.4 |
| | ≤1.0% aldehyde | 0.7 | 0.4 | 0.5 |
| GD release | | Pass | Pass | Pass |
| Uniformity | 85.0-115.0% Label Strength (LS) | 97.0% | 97.1% | 98.0% |
| | Stage 1 (n = 10): If one unit is outside the range and between 75% and | all values within | all values within | all values within |

TABLE 2-continued

In Process Controls for the second extrusion

| | | Batch number | | |
|---|---|---|---|---|
| | | 03J001 | 03H004 | 03M001 |
| | | | Batch size | |
| Parameter | Specifications | 80 g | 80 g | 80 g |
| | 125% LS or RSD ≥ 6.0%, test 20 more units. Stage 2 (n = 20): pass if no more than 1 unit is outside the range, and is between 75% and 125% LS, and the RSD ≤ 7.8%. | range | within range | range |

Example 4

Treatment of Macular Edema with a GD Implant

A 58 year old man diagnosed with cystic macular edema treated by administration of a biodegradable drug delivery system administered to each eye of the patient. A 2 mg intravitreal implant containing about 1000 µg of PLGA and about 1000 µg of beclomethasone dipropionate is placed in his left eye at a location that does not interfere with the man's vision. A similar implant is administered subconjunctivally to the patient's right eye. A more rapid reduction in retinal thickness in the right eye appears to be due to the location of the implant and the activity of the steroid. After about 3 months from the surgery, the man's retinal appears normal, and degeneration of the optic nerve appears to be reduced. No increase in intraocular pressure is seen one week after administration.

Example 5

Treatment of ARMD with a GD Composition

A 62 year old woman with wet age-related macular degeneration is treated with an intravitreal injection of 100 µl of a hyaluronic acid solution containing about 1000 µg of fluticasone propionate crystals in suspension. Within one month following administration the patient exhibits an acceptable reduction in the rate of neovascularization and related inflammation. The patient reports an overall improvement in quality of life.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

What is claimed is:

1. An ophthalmic composition comprising: a therapeutically effective amount of a Glucocorticoid Derivative (GD) comprising an acyl group linked to $C_{17}$, $C_{21}$, or combination thereof via an ester linkage, and a viscosity-inducing component.

2. The composition of claim 1 wherein said GD has a lipophilicity greater than 2.53.

3. The composition of claim 1 wherein said GD has an aqueous solubility less than 10 mg/ml.

4. The composition of claim 1, wherein the viscosity-inducing component comprises hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

5. The composition of claim 4, wherein the viscosity-inducing component comprises a polymeric hyaluronate component.

6. The composition of claim 1 wherein said acyl group is selected from the group consisting of an acetyl, butyryl, valeryl, propionyl, furoyl, and benzoyl group.

7. The composition of claim 1 wherein said composition is suitable for administration to a patient by at least one of intravitreal administration and periocular administration.

8. The composition of claim 1 wherein said ophthalmic composition is an implant.

9. The composition of claim 8 wherein said implant further comprises a polymeric component.

10. The composition of claim 9 wherein said polymeric component is selected from the group consisting of poly (lactide-co-glycolide) polymer (PLGA), poly-lactic acid (PLA), poly-glycolic acid (PGA), polyesters, poly (ortho ester), poly(phosphazine), poly (phosphate ester), polycaprolactones, gelatin, and collagen, and derivatives and combinations thereof.

11. The composition of claim 1, wherein the GD is beclomethasone propionate.

12. The composition of claim 1, wherein the GD is beclomethasone dipropionate.

* * * * *